US012702408B2

(12) United States Patent
Mazzoni et al.

(10) Patent No.: US 12,702,408 B2
(45) Date of Patent: Aug. 11, 2026

(54) RIGID STERILE BARRIER

(71) Applicant: CILAG GMBH INTERNATIONAL, Zug (CH)

(72) Inventors: Anna Mazzoni, Hamburg (DE); Christiane Eichenseer, Hamburg (DE); Denise Griffiths, Hamburg (DE); Nicholas Layman, Cincinnati, OH (US); John P. Soehnlen, Cincinnati, OH (US); Rebecca Morgenroth, Hamburg (DE)

(73) Assignee: CILAG GMBH INTERNATIONAL, Zug (CH)

( * ) Notice: Subject to any disclaimer, the term of this patent is extended or adjusted under 35 U.S.C. 154(b) by 79 days.

(21) Appl. No.: 18/901,915

(22) Filed: Sep. 30, 2024

(65) Prior Publication Data

US 2026/0090802 A1 Apr. 2, 2026

(51) Int. Cl.

*A61B 17/068* (2006.01)
*A61B 50/30* (2016.01)
*A61B 50/33* (2016.01)

(52) U.S. Cl.

CPC ............ *A61B 17/068* (2013.01); *A61B 50/33* (2016.02); *A61B 2017/0688* (2013.01); *A61B 2050/3004* (2016.02)

(58) Field of Classification Search

CPC ............ A61B 17/07292; A61B 17/115; A61B 2017/0688; A61B 2017/07257; A61B 2017/07271; A61B 2017/07285; A61B 2050/0065; A61B 50/30; A61B 50/33

See application file for complete search history.

(56) References Cited

U.S. PATENT DOCUMENTS 5,820,956 A * 10/1998 Hatakeyama ........... B32B 27/34 428/476.3
2012/0305426 A1* 12/2012 Valaie ..................... B65B 55/02 53/425
2017/0224432 A1* 8/2017 Döring ............... B65D 77/0433
2020/0016323 A1 1/2020 Rault et al.
2020/0205824 A1* 7/2020 Barton .................. A61B 50/30

OTHER PUBLICATIONS

International Search Report and Written Opinion mailed Nov. 28, 2025 in corresponding International Patent Application No. PCT/IB2025/059835.

* cited by examiner

*Primary Examiner* — Mohamed G Gabr
(74) *Attorney, Agent, or Firm* — Troutman Pepper Locke LLP

(57) ABSTRACT

A rigid sterile barrier for protecting and maintaining a sterile environment for a medical device is disclosed. The rigid sterile barrier comprises a thermoformed tray and a top foil comprising a desiccant.

17 Claims, 8 Drawing Sheets

RIGID STERILE BARRIER

FIELD

The present disclosure generally relates to a rigid sterile barrier for oxygen and moisture sensitive products. More specifically, the present disclosure relates to a rigid sterile barrier for maintaining a sterile environment for a medical device.

BACKGROUND

A sterile environment must be maintained for medical devices used in surgical procedures during transportation from the facility which they are manufactured to the operating room. It is also important that the medical device is protected during transportation to avoid damage. Weight and size of packaging may affect the cost of transportation and should also be considered. A rigid sterile barrier may include a tray and top foil encasing a medical device providing a lightweight solution to maintain a sterile environment and protect the medical device from damages.

SUMMARY

It is an object of the present designs to provide devices and methods to meet the above-stated needs. The designs can be for systems for assuring protection and maintaining a sterile environment for a medical device before being used in surgery.

The disclosed technology includes a rigid sterile barrier. The rigid sterile barrier may include a thermoformed tray with a cavity, a lip extending above and around the cavity's perimeter, and a flange extending around the lip. An oxygen scavenger may be placed at the bottom of the cavity. A top foil may be adhered to the lip of the tray. The top foil may be non-permeable and may contain a desiccant integrated into at least one layer of the top foil. The desiccant in the top foil may include calcium oxide.

The top foil may include an aluminum layer. The cavity may not contain an additional desiccant, and the thermoformed tray may not have an additional desiccant or oxygen scavenger integrated into it. Similarly, the top foil may not have an additional oxygen scavenger integrated into it.

Both the thermoformed tray and the top foil may be non-permeable. The cavity may be filled with an inert gas, which may be nitrogen.

The medical device may be positioned between the oxygen scavenger and the top foil. The oxygen scavenger may be thermally welded to the bottom of the cavity in the thermoformed tray. The medical device may be a surgical staple cartridge, which may have a length of approximately 100 millimeters, a width of approximately 45 millimeters, and a thickness of approximately 16 millimeters.

Other aspects of the present disclosure will become apparent upon reviewing the following detailed description in conjunction with the accompanying figures. Additional features or manufacturing and use steps can be included as would be appreciated and understood by a person of ordinary skill in the art.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combine elements from multiple figures to better suit the needs of the user.

DETAILED DESCRIPTION

Specific examples of the present invention are now described in detail with reference to the Figures, where identical reference numbers indicate elements which are functionally similar or identical. The examples provide solutions for transporting and protecting medical devices. A thermoformed tray and a protective top foil forming a rigid protective barrier to provide a cavity for protecting a medical device to be used during a surgical procedure. The rigid sterile barrier also maintains a sterile environment for a medical device during transportation. In some examples, the medical device is a surgical staple cartridge reload for a surgical stapler.

The invention is not necessarily limited to the examples described, which can be varied in construction and detail. As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 71% to 99%.

Figure 1:
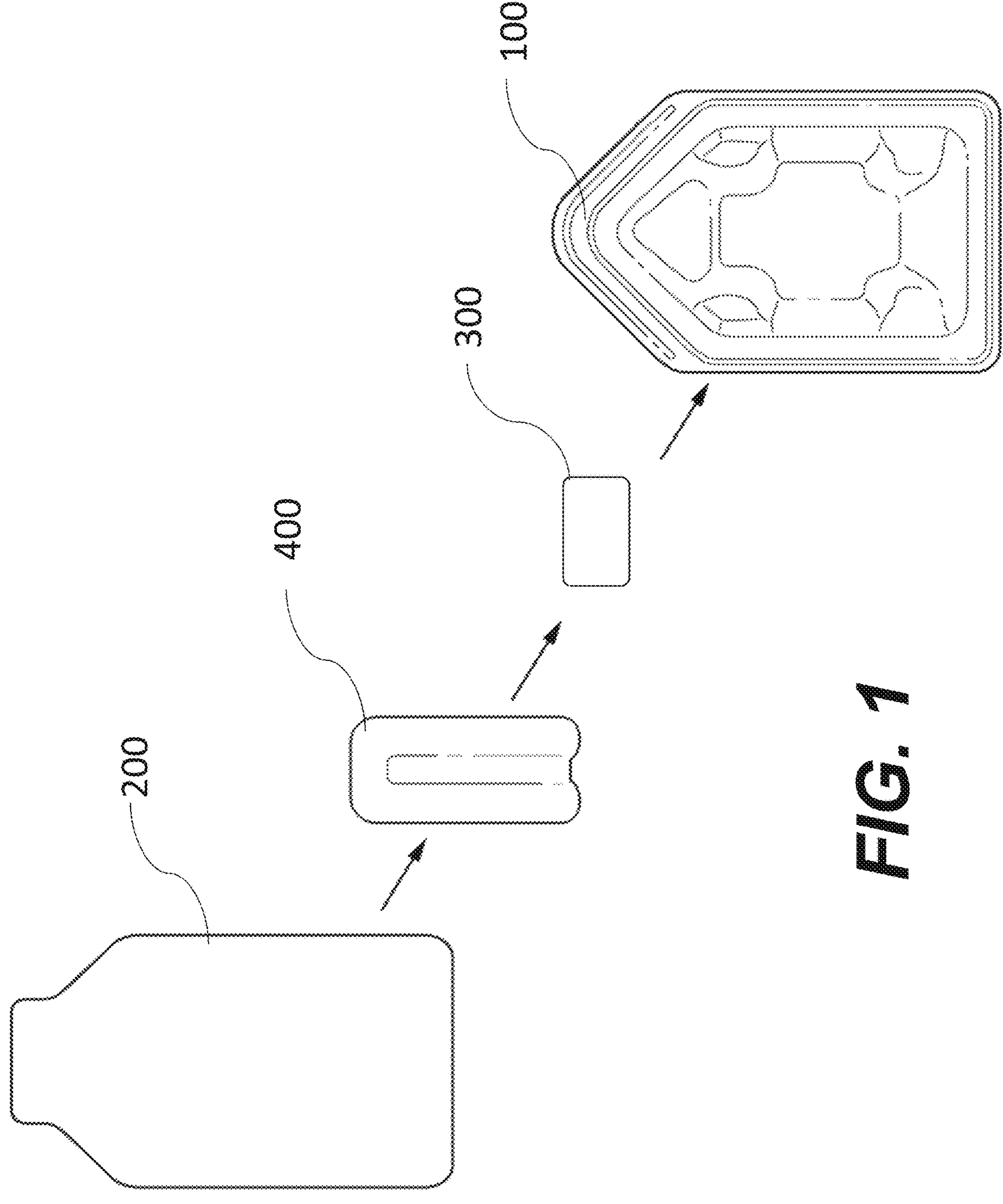
FIG. 1 is an exploded view of a rigid sterile barrier formed by a tray and top foil enclosing a medical device and an oxygen scavenger, according to aspects of the present invention.
Figure 2:
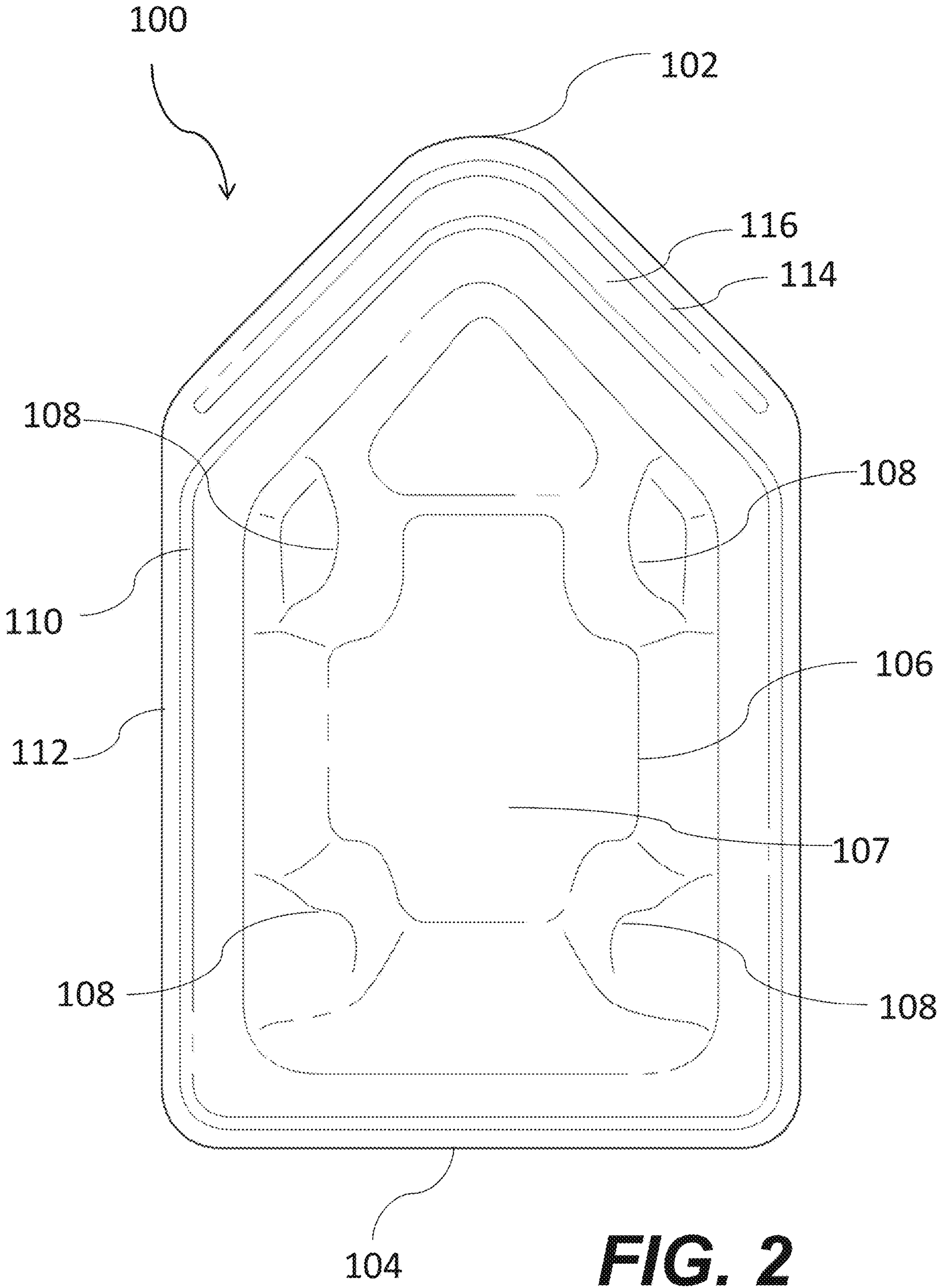
FIG. 2 is a top view of a tray component of a rigid sterile barrier, according to aspects of the present invention.

With reference to FIG. 1, in some examples, a rigid sterile barrier comprises a thermoformed tray 100 and a top foil 200 which are adhered or otherwise attached (e.g., by thermal welding, heat staking, etc.) together to form an enclosed volume to retain and protect a medical device 400. In some examples, an oxygen scavenger 300 is disposed within the rigid sterile barrier to remove residual oxygen which may cause unwanted reactions (e.g., oxidization) with the medical device 400 enclosed within. In some examples, the oxygen scavenger 300 is disposed at the bottom of the tray 100 and medical device 400 rests on top of the oxygen scavenger 300. In some examples, the medical device abuts the bottom of the top foil 200.

In some examples, the rigid sterile barrier comprises a length of approximately 190 millimeters. In some examples, the rigid sterile barrier comprises a width of approximately 120 millimeters. In some examples, the rigid sterile barrier comprises a thickness of approximately 30 millimeters.

In some examples, the medical device is sealed within rigid sterile barrier (i.e., the top foil 200 is adhered to the tray 100) under an inert gas, such that the inert gas is retained with the rigid sterile barrier until it is opened. The inert gas may be nitrogen or another suitable inert gas to maintain a sterile, protective environment for the medical device 400. As further discussed herein, the top foil 200 may comprise a desiccant layer integrated into the top foil to remove moisture/humidity within the rigid sterile barrier. As such, no further desiccant may be provided within the rigid sterile barrier. Separation of the desiccant and the oxygen scavenger may allow for faster absorption rates of both oxygen and moisture compared to products which combine a desiccant and oxygen scavenger in a single material. As a non-limiting example, the oxygen scavenger 300 does not necessarily need desiccant properties, and as such it is contemplated that the oxygen scavenger 300 is limited to removing oxygen from the sealed space defined by the tray 100 and the top foil 200.

With reference to FIGS. 2-5, according to some aspects, the tray 100 comprises cavity 106 for receiving and retaining a medical device 400. The tray may further comprise a lip 110 extending disposed around and extending above the cavity 106. The top foil 200 may be adhered to the lip 110 of the tray 100. A flange 112 may extend outwardly around the lip 110.

Figure 4:
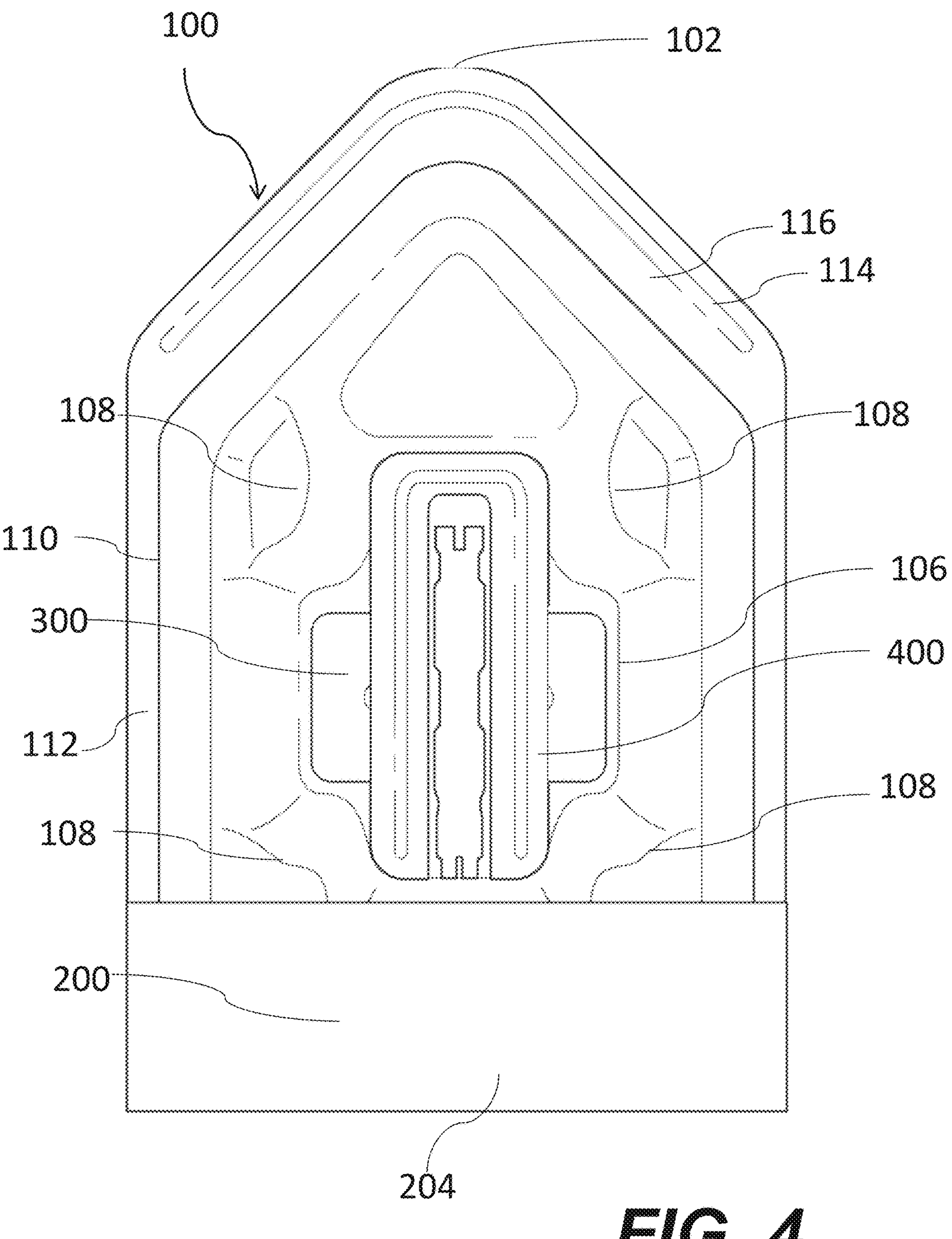
FIG. 4 is a top view of a tray component of a rigid sterile barrier with a protective top foil being partial peeled from the tray and an oxygen scavenger and medical device disposed within, according to aspects of the present invention.
Figure 5:
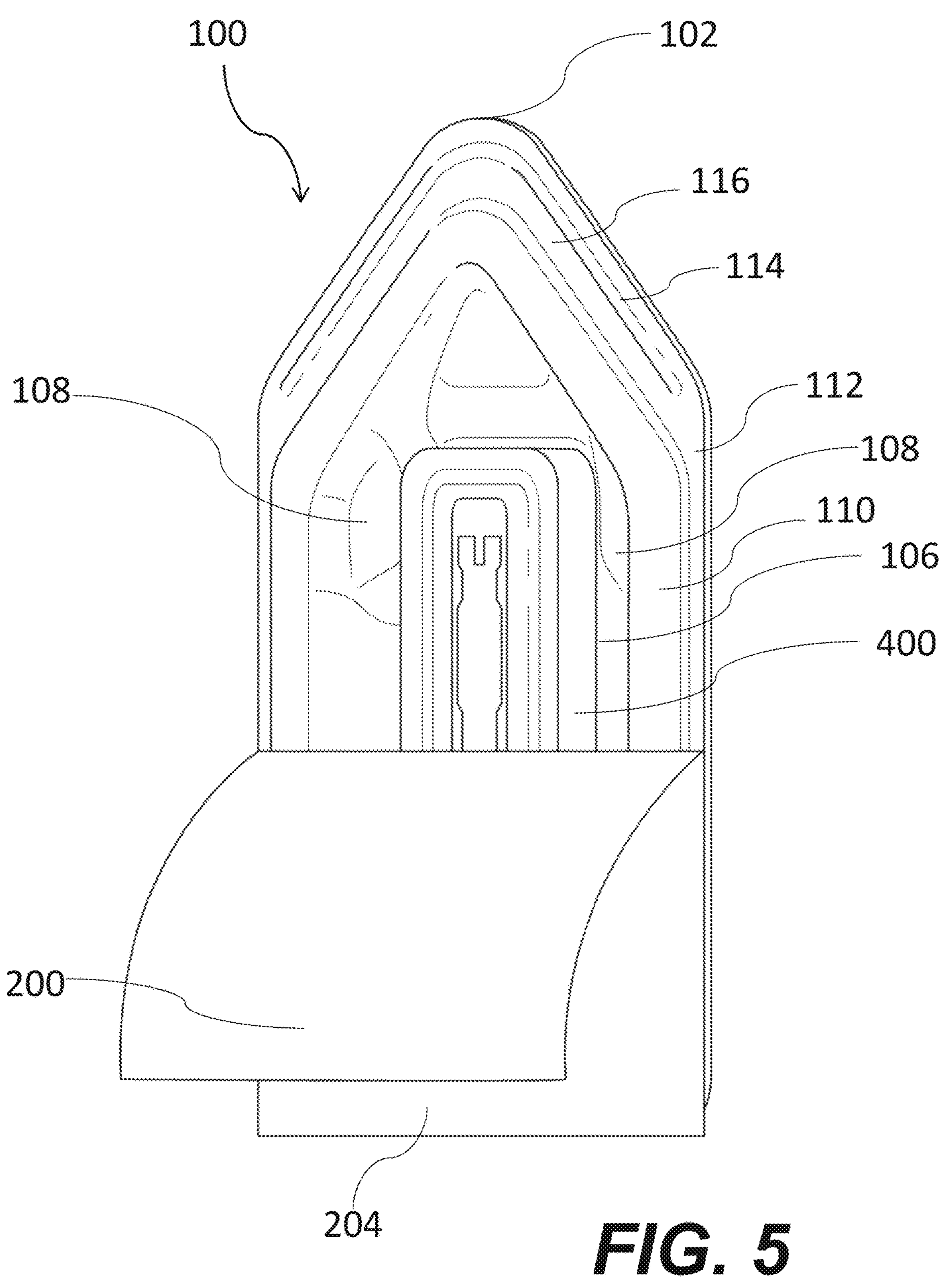
FIG. 5 is a perspective view of a tray component of a rigid sterile barrier with a protective top foil being partial peeled from the tray and an oxygen scavenger and medical device disposed within, according to aspects of the present invention.

In some examples, the first end 102 of the thermoformed tray 100 comprises a ridge 114. In some examples, a space 116 is provided between the lip 110 and the ridge 114. The ridge 114 may facilitate removal of the top foil 200 from the tray 100 (as depicted in FIGS. 4 and 5). The ridge 114 may be grasped with one hand, while the top foil 200 is grasped with another.

In some examples, the thermoformed tray 100 is substantially pentagonal in shape and comprises a substantially triangular-shaped first end 102 and a substantially rectangular-shaped second end 104. In some examples, the cavity 106 of the thermoformed tray 100 comprises four dimples 108, each dimple 108 located in a corner of the substantially rectangular-shaped second end 104. In some examples, the four dimples 108 are retain the medical device 400 within the cavity 106 of the thermoformed tray 100. In some examples, the corners of the medical device 400 abut the dimples 108. In some examples, the dimples 108 are spaced approximately 45 mm apart to accommodate the width of the medical device 400.

Figure 7:
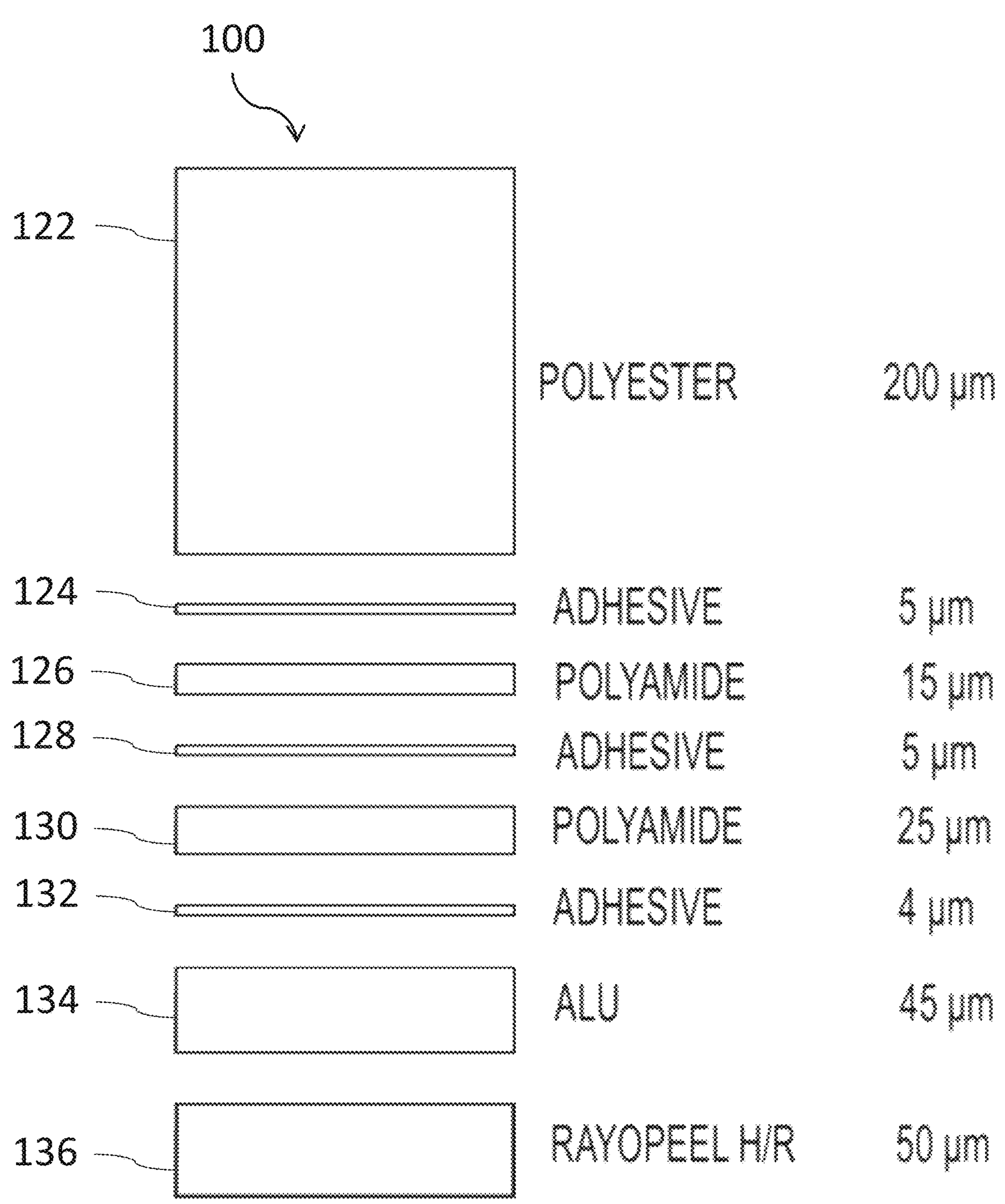
FIG. 7 is a schematic of the layers of a tray component of a rigid sterile barrier, according to aspects of the present invention.

With reference to FIG. 7, in some examples, the thermoformed tray may comprise five separate material layers, not include adhesive layers. In some examples, thermoforming of the tray provided a consistent thickness throughout the tray. It will be appreciated that "thickness" of the tray refers to the thickness of the thermoformed material of the tray, not to the height of the tray as formed. In some examples, the tray is at least 300 microns thick to provide adequate protection for the medical device during transportation. In some examples, the tray is approximately 350 microns thick. In some examples, the thermoformed tray comprises a polyester layer 122, a first polyamide layer 126, a second polyamide layer 130, an aluminum layer 134, and a sealing layer 136 for adhesion of the top foil to the tray (e.g., a Rayopeel layer, as disclosed herein). In some examples, the first polyamide layer 126 and the second polyamide layer 130 each comprise oriented polyamide. In some examples, the first polyamide layer 126 is oriented orthogonal to the second polyamide layer 130.

In some examples, the sealing layer 136 comprises a multipolymer blend (e.g., Rayopeel™). In some examples, the sealing layer comprises a top foil formed by a heat-sealable rigid polymer, a non-heatsealable polymer which does not form a solution with the heat-sealable rigid polymer, a heat-scalable branched olefinic polymer, and an additional polymer compatible with the heat-sealable rigid polymer, the non-heatsealable polymer, and the heat-scalable branched olefinic polymer. In some examples, sealing layer comprises about 20 to about 80% by weight of the heat-scalable rigid polymer, about 0.1 to about 50% by weight of the non-heatsealable polymer, about 0.1 to about 30% by weight of the heat-sealable branched olefinic polymer, and about 0% to about 45% the additional polymer. In some examples, the heat-sealable rigid polymer comprises polyethylene, polypropylene, polybutene, polyamide, polyvinyl chloride, or a combination thereof. In some examples, the non-heatsealable polymer comprises a styrene-butadiene copolymer. In some examples, the heat-sealable branched olefinic polymer comprises polyethylene. In some examples, the additional polymer comprises an ethylene-alkylacrylate copolymer.

In some examples, the thermoformed tray further comprises a first adhesive layer 124 between the polyester layer 122 and the first polyamide layer 126, a second adhesive layer 128 between the first polyamide layer 126 and the second polyamide layer 130, and a third adhesive layer 132 between the second polyamide layer 130 and the aluminum layer 134. In some examples, the polyester layer 122 is approximately 200 microns thick and has a mass per area of approximately 254 grams per square meter, the first polyamide layer 126 is approximately 15 microns thick and has a mass per area of approximately 17 grams per square meter, the second polyamide layer 130 is approximately 25 microns thick and has a mass per area of approximately 29 grams per square meter, the aluminum layer 134 is approximately 45 microns thick and has a mass per area of approximately 122 grams per square meter, and sealing layer (or Rayopeel™ layer) 136 is approximately 50 microns thick and has a mass per area of approximately 47 grams per square meter.

Figure 6:
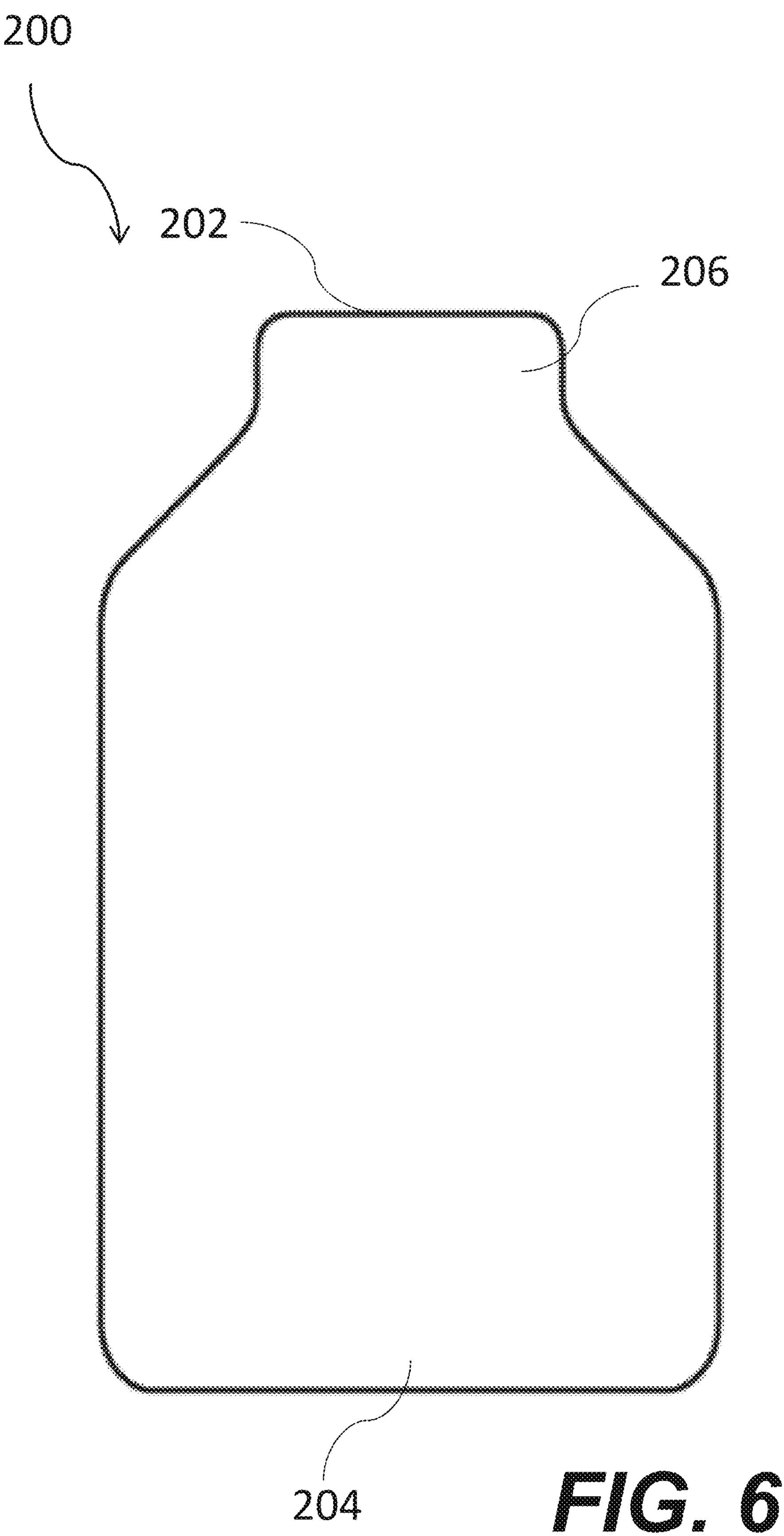
FIG. 6 is a top view of a top foil component of a rigid sterile barrier, according to aspects of the present invention.

FIG. 6 depicts the top foil 200, according to some examples. In some examples, the top foil 200 comprises a first end 202 and a second end 204. In some examples, the first end 202 of the top foil 200 comprises a tab 206. The tab 206 may extend outwardly from the first end of the tray (e.g., the first end 102 of the tray 100 as depicted if FIGS. 2-5) when the top foil is adhered or otherwise attached to the tray to provide a portion of the top foil 200 to be grasped, thereby facilitating peeling of the top foil from the tray. The other portions of the top foil 200 may be substantially aligned with the flange 112 of the tray when the top foil is adhered to the tray.

In some examples, the top foil is non-permeable and provided to be resistant to puncture. In some examples, the top foil 200 is at least 50 microns thick. In some examples, the top foil 200 is between 60 microns and 100 microns. In some examples, the top foil 200 is between 70 microns and 80 microns. In some examples, the top foil 200 is at least 80 microns thick. In a preferred example, the top foil 200 is between 90 and 100 microns thick, and more preferably 93 microns thick.

Figure 8:
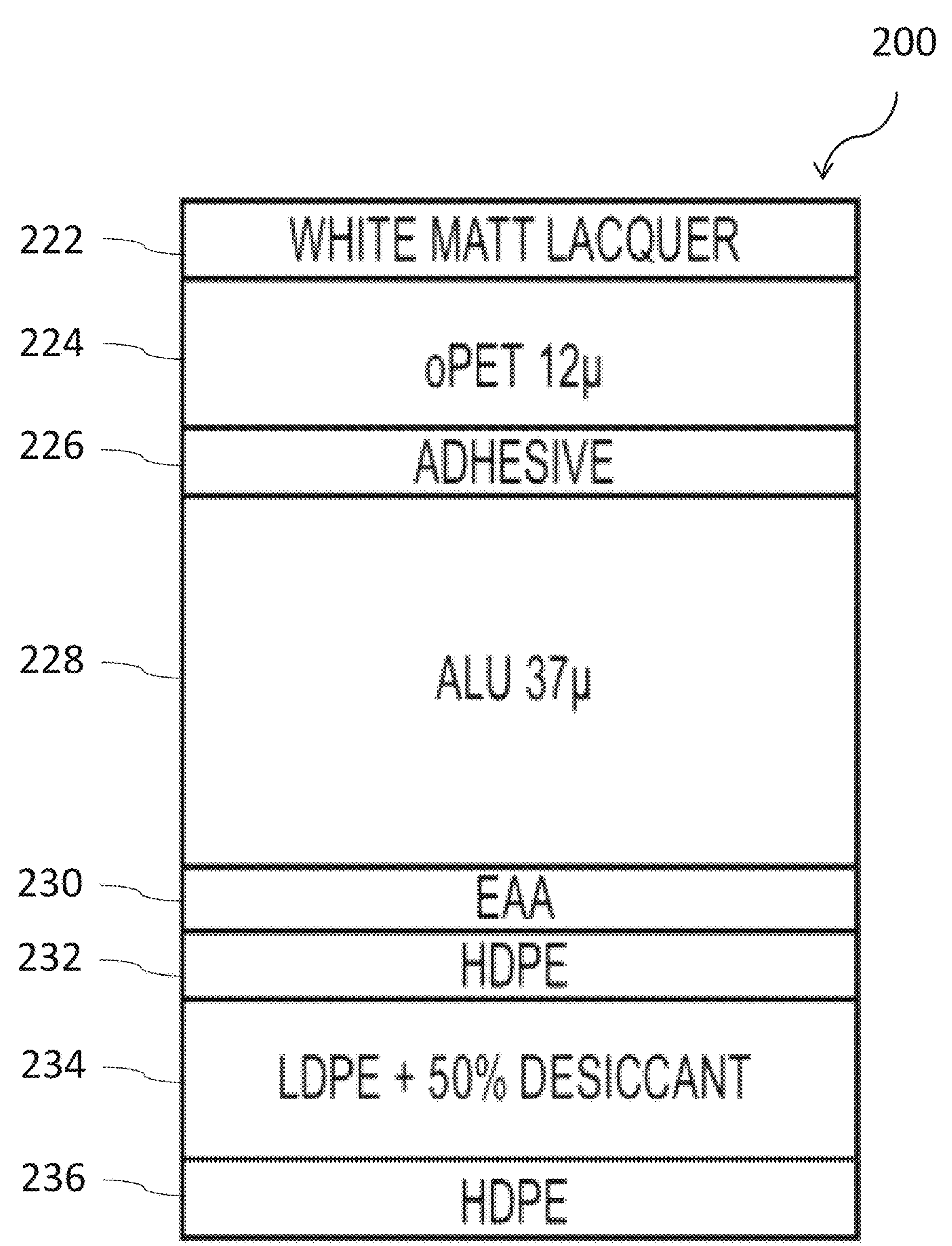
FIG. 8 is a schematic of the layers of a top foil component of a rigid sterile barrier, according to aspects of the present invention.

With reference to FIG. 8, in some examples, the top foil 200 comprises a white lacquer layer 222 is approximately 2 microns thick and has a mass per area of approximately 2 grams per square meter, the oriented polyester layer 224 is approximately 12 microns thick and has a mass per area of approximately 17 grams per square meter, the aluminum layer 228 is approximately 37 microns thick and has a mass per area of approximately 100 grams per square meter, and the polyethylene layer 234 is approximately 42 microns thick and has a mass per area of approximately 53 grams per square meter.

In some examples, the white lacquer layer 222 as an outermost layer. In some examples, inside of the white lacquer layer 222, the top foil 200 comprises an oriented polyester layer 224, an aluminum layer 228, and a polyethylene layer 234. In some examples, and adhesive layer 226 is provided between the oriented polyester layer 224 and the aluminum layer 228. In some examples, an ethylene acrylic acid (EAA) adhesive layer 230 is provided between the aluminum layer 228 and the polyethylene layer 234.

In some examples, the polyethylene layer 234 of the top foil comprises a desiccant. In some examples, the polyethylene layer 234 of the top foil comprises approximately 50 percent by weight of low-density polyethylene and approximately 50 percent by weight of the desiccant. In some examples, the desiccant comprises calcium oxide. Since the top foil comprises a desiccant, no additional desiccant may be provided within the rigid sterile barrier, the cavity of the tray, or integrated into the tray.

In some examples, the polyethylene layer 234 comprises low-density polyethylene layer 234, comprising the desiccant and sandwiched between a first high density polyethylene layer 232 and a second high density polyethylene layer 236. An ethylene acrylic acid (EAA) adhesive layer 230 may be provided between the aluminum layer 228 and first high density polyethylene layer 232.

Figure 3:
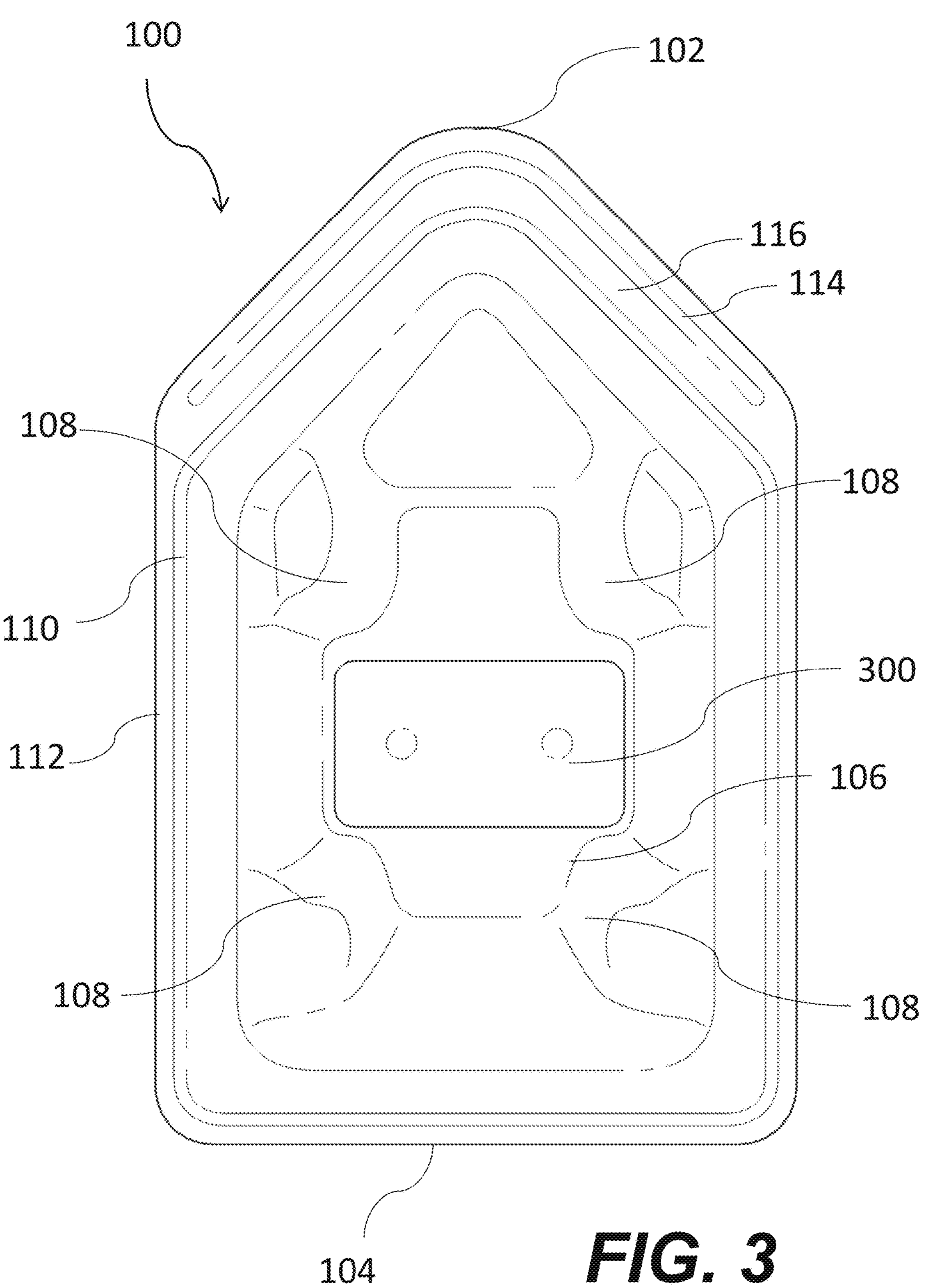
FIG. 3 is a top view of a tray component of a rigid sterile barrier and an oxygen scavenger disposed within, according to aspects of the present invention.

With reference to FIG. 3, in some examples, the packaging container further comprises an oxygen scavenger 300. The oxygen scavenger 300 may be thermally welded to a bottom 107 of the cavity 106 of the thermoformed tray 100. In some examples, the medical device 400 rests on top of the oxygen scavenger 300 when disposed within the cavity 106 of the thermoformed tray 100. Since an oxygen scavenger 300 is provided within the rigid sterile barrier, when sealed, the tray or the top foil may not require a supplemental oxygen scavenger, thereby making the tray 100 smaller for storage and shipment. In some examples, the dimples 108 provided towards the first end 102 of the tray 100 are spaced apart from the dimples 108 provided towards the second end 104 of the tray 100 at a distance approximately equal to the width of the oxygen scavenger 300.

Additional views of an example tray 100 are shown in U.S. Design Ser. No. 29/965,947, entitled Rigid Sterile Barrier System, filed Sep. 30, 2024, the entire contents of which is hereby incorporated by reference in its entirety for all purposes.

Examples of the present disclosure can be implemented by any of the following numbered clauses:

Clause 1: A rigid sterile barrier for a medical device (400): a thermoformed tray (100) comprising: a cavity (106); a lip (110) extending above and disposed around a perimeter of the cavity; and a flange (112) extending around the lip (110); an oxygen scavenger (300) disposed in a bottom (107) of the cavity (106); and a top foil (200) adhered to the lip (110) of the thermoformed tray, the top foil (200) being non-permeable and comprising a desiccant.

Clause 2: The rigid sterile barrier of Clause 1, wherein the desiccant comprises calcium oxide.

Clause 3: The rigid sterile barrier of Clauses 1 or 2, wherein the medical device (400) is disposed between the oxygen scavenger and the top foil (200).

Clause 4: The rigid sterile barrier of any one of Clauses 1 to 3, wherein the oxygen scavenger is thermally welded to the bottom (107) of the cavity (106) of the thermoformed tray (100).

Clause 5: The rigid sterile barrier of any one of Clauses 1 to 4, wherein the thermoformed tray (100) comprises an aluminum layer (134).

Clause 6: The rigid sterile barrier of any one of Clauses 1 to 5, wherein the thermoformed tray (100) is at least 300 microns thick.

Clause 7: The rigid sterile barrier of any one of Clauses 1 to 6, wherein the thermoformed tray (100) is at approximately 350 microns thick.

Clause 8: The rigid sterile barrier of any one of Clauses 1 to 7, wherein the top foil (100) is approximately 90 microns thick.

Clause 9: The rigid sterile barrier of any one of Clauses 1 to 8, wherein the top foil (200) comprises an aluminum layer (228).

Clause 10: The rigid sterile barrier of any one of Clauses 1 to 9, wherein the medical device (400) is a surgical staple cartridge.

Clause 11: The rigid sterile barrier of Clause 10, wherein the surgical staple cartridge comprises a length of approximately 100 millimeters, a width of approximately 45 mm, and a thickness of approximately 16 millimeters.

Clause 12: The rigid sterile barrier of any one of Clauses 1 to 11, wherein the cavity (106) does not comprise an additional desiccant.

Clause 13: The rigid sterile barrier of any one of Clauses 1 to 12, wherein the thermoformed tray (100) does not comprise an additional desiccant integrated into the thermoformed tray (100).

Clause 14: The rigid sterile barrier of any one of Clauses 1 to 13, wherein the thermoformed tray (100) does not comprise an additional oxygen scavenger integrated into the thermoformed tray (100).

Clause 15: The rigid sterile barrier of any one of Clauses 1 to 14, wherein the top foil (200) does not comprise an additional oxygen scavenger integrated into the top foil (200).

Clause 16. The rigid sterile barrier of any one of Clauses 1 to 15, wherein the cavity (106) is filled with an inert gas.

Clause 17: The rigid sterile barrier of Clause 16, wherein the inert gas is nitrogen.

In describing example embodiments, terminology has been resorted to for the sake of clarity. As a result, not all possible combinations have been listed, and such variants are often apparent to those of skill in the art and are intended to be within the scope of the claims which follow. It is intended that each term contemplates its broadest meaning as understood by those skilled in the art and includes all technical equivalents that operate in a similar manner to accomplish a similar purpose without departing from the scope and spirit of the invention. It is also to be understood that the mention of one or more steps of a method does not preclude the presence of additional method steps or intervening method steps between those steps expressly identified. Similarly, some steps of a method can be performed in a different order than those described herein without departing from the scope of the disclosed technology.

What is claimed is:

1. A rigid sterile barrier for a medical device (400):

a thermoformed tray (100) comprising:

a cavity (106);

a lip (110) extending above and disposed around a perimeter of the cavity; and a flange (112) extending around the lip (110);

an oxygen scavenger (300) disposed in a bottom (107) of the cavity (106); and a top foil (200) adhered to the lip (110) of the thermoformed tray, the top foil (200) being non-permeable and comprising a desiccant, wherein the desiccant is integrated into a first polymer layer of the top foil, and wherein the first polymer layer comprising the desiccant is positioned between a second polymer layer and a third polymer layer, the second polymer layer and the third polymer layer having higher densities than the first polymer layer.

2. The rigid sterile barrier of claim 1, wherein the desiccant comprises calcium oxide.

3. The rigid sterile barrier of claim 1, wherein the medical device (400) is configured to be disposed between the oxygen scavenger and the top foil (200).

4. The rigid sterile barrier of claim 1, wherein the oxygen scavenger is thermally welded to the bottom (107) of the cavity (106) of the thermoformed tray (100).

5. The rigid sterile barrier of claim 1, wherein the thermoformed tray (100) comprises an aluminum layer (134).

6. The rigid sterile barrier of claim 1, wherein the thermoformed tray (100) is at least 300 microns thick.

7. The rigid sterile barrier of claim 1, wherein the thermoformed tray (100) is at approximately 350 microns thick.

8. The rigid sterile barrier of claim 1, wherein the top foil (100) is approximately 90 microns thick.

9. The rigid sterile barrier of claim 1, wherein the top foil (200) comprises an aluminum layer (228).

10. The rigid sterile barrier of claim 1, further comprising the medical device, and wherein the medical device (400) is a surgical staple cartridge.

11. The rigid sterile barrier of claim 10, wherein the surgical staple cartridge comprises a length of approximately 100 millimeters, a width of approximately 45 mm, and a thickness of approximately 16 millimeters.

12. The rigid sterile barrier of claim 1, wherein the cavity (106) does not comprise an additional desiccant.

13. The rigid sterile barrier of claim 1, wherein the thermoformed tray (100) does not comprise an additional desiccant integrated into the thermoformed tray (100).

14. The rigid sterile barrier of claim 1, wherein the thermoformed tray (100) does not comprise an additional oxygen scavenger integrated into the thermoformed tray (100).

15. The rigid sterile barrier of claim 1, wherein the top foil (200) does not comprise an additional oxygen scavenger integrated into the top foil (200).

16. The rigid sterile barrier of claim 1, wherein the cavity (106) is filled with an inert gas.

17. The rigid sterile barrier of claim 16, wherein the inert gas is nitrogen.

* * * * *